United States Patent [19]

Rich et al.

[11] Patent Number: 4,573,467
[45] Date of Patent: Mar. 4, 1986

[54] OPTICAL COUPLING DEVICE FOR BIOMICROSCOPE

[75] Inventors: Alan H. Rich, Ft. Washington; Douglas E. Gaasterland, Potomac; Thomas E. Tedder, Silver Spring, all of Md.

[73] Assignee: The United States of America as represented by the Department of Health and Human Services, Washington, D.C.

[21] Appl. No.: 494,378

[22] Filed: May 13, 1983

[51] Int. Cl.[4] .................... A61B 17/36; A61N 5/00
[52] U.S. Cl. .................... 128/303.1; 128/395; 219/121 LQ; 219/121 LR
[58] Field of Search .................... 128/303.1, 395–398; 219/121 LQ, 121 LR, 121 LW

[56] References Cited

U.S. PATENT DOCUMENTS

| | | | |
|---|---|---|---|
| 3,659,613 | 5/1972 | Bredemeier | 128/395 |
| 3,703,176 | 11/1972 | Vassiliadis et al. | 128/395 |
| 3,769,963 | 11/1973 | Goldman et al. | 128/303.1 |
| 3,796,220 | 3/1974 | Bredemeier | 128/303.1 |
| 3,828,788 | 8/1974 | Krasnov et al. | 128/303.1 |
| 4,123,143 | 10/1978 | Yachin et al. | 128/303.1 |
| 4,141,362 | 2/1979 | Wurster | 128/303.1 |
| 4,164,222 | 8/1979 | Prokhowv et al. | 128/303.1 |
| 4,309,998 | 1/1982 | Rose et al. | 128/303.1 |
| 4,396,285 | 8/1983 | Presta et al. | 128/303.1 |
| 4,397,310 | 8/1983 | Pomerantzeff | 128/303.1 |

FOREIGN PATENT DOCUMENTS

| | | | |
|---|---|---|---|
| 69987 | 1/1983 | European Pat. Off. | 128/303.1 |
| 3043533 | 6/1981 | Fed. Rep. of Germany | 128/303.1 |

*Primary Examiner*—Lee S. Cohen
*Attorney, Agent, or Firm*—Holman & Stern

[57] ABSTRACT

An apparatus is provided for permitting high power laser pulses to be controllably focused in the center of a biomicroscope field of observation by means of a mirror movable in three dimensions. The shutter mechanism, synchronized to the generation of each laser pulse, closes to protect the eyes of an observer against damage from the laser. The mirror is mounted on a shaft disposed on a housing for movement longituinally of its axis, rotationally about that axis, and pivotably about a point on the axis. The apparatus is portable so as to be easily transported to various locations in a medical facility.

15 Claims, 5 Drawing Figures

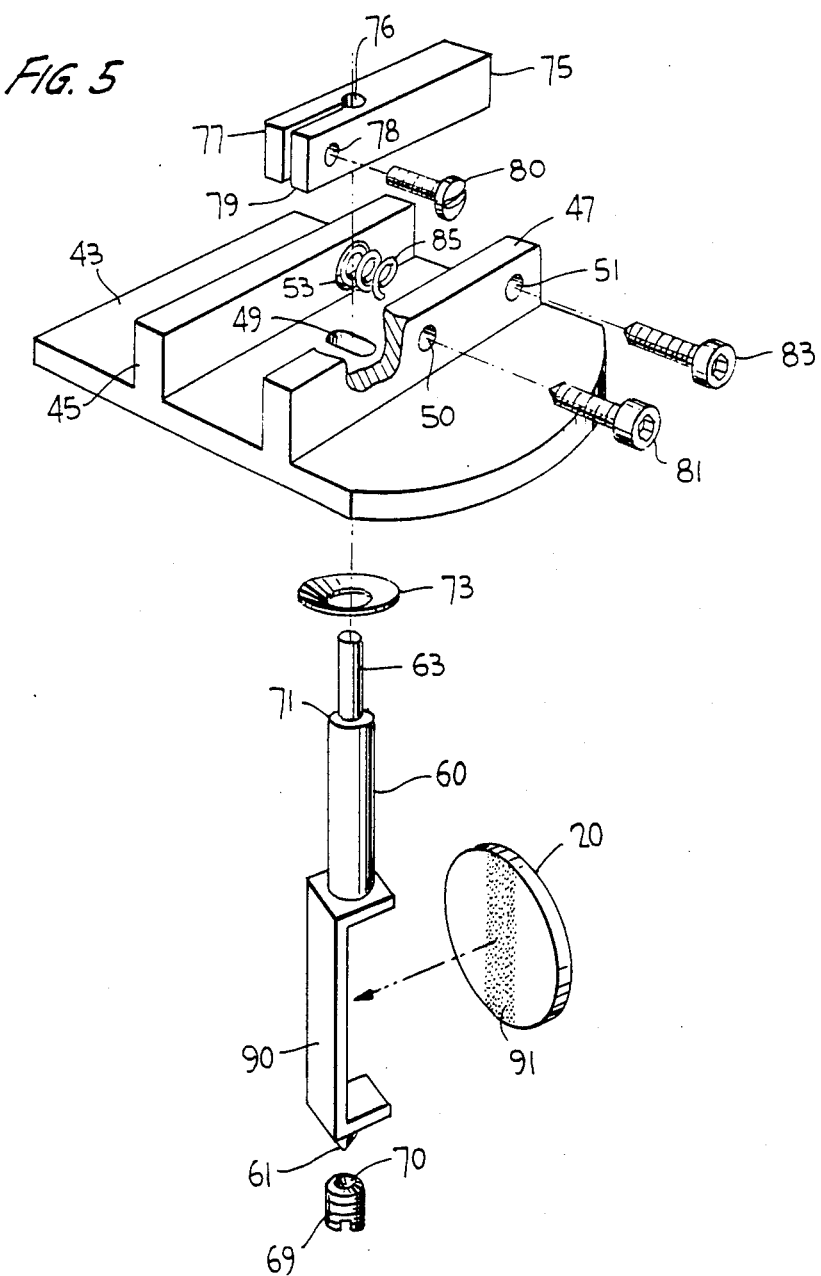

OPTICAL COUPLING DEVICE FOR BIOMICROSCOPE

BACKGROUND OF THE INVENTION

1. Technical Field

The present invention relates generally to the delivery of Q-switched high power laser pulses for purposes of medical treatment. More specifically, the invention relates to a method and apparatus for use with a biomicroscope which permits high power laser pulses to be focused coincident with the center line and focus of the biomicroscope while protecting the eyes of the biomicroscope observer.

2. The Prior Art

There has been increasing interest in the possibility of applying high power pulsed laser energy to tissue for the purpose of treating various diseases. In such systems, use is made of the very small focal diameter of laser beams to achieve high power density in the target tissue. A requirement of the laser delivery portion of the system is that the focused beam must be delivered coincident with the center of the field of observation of a biomicroscope. This is particularly important in the treatment of ocular tissue where the area to be treated may be no larger than one hundred and fifty micrometers in diameter. When high power laser pulses are applied to this tissue, an error in the application site of 0.1 millimeters can result in undesirable damage to adjacent tissue instead of beneficial alteration of the target tissue. The treating physician must therefore be able to predict, with a high degree of accuracy, where the pulse of energy will intersect the tissue. Prior art biomicroscopes allow adequate observation of sites to be treated; however, the problem which has been encountered is to couple high energy laser pulses to the observation system so that the focal point and the center of the observation system coincide with the focal point of the laser pulse. Once this has been done, there remains the problem of simply and effectively protecting the eyes of the observer from the high power laser pulses.

Another problem with systems of the type described relates to mobility. Mobility is an important feature of these systems, particularly where they are intended for ocular treatment. It is desirable that the system be readily transportable anywhere in a hospital or other medical facility.

It is to be noted that the present invention, when applied to surgery in the eye, relates to surgical procedures performed anterior of the retina and using high energy laser pulses. This is to be distinguished from photo coagulation procedures performed on the retina with low power CW (continuous wave) lasers such as described in U.S. patent application Ser. No. 06/239,015, now U.S. Pat. No. 4,397,310 filed February 27, 1981 by Oleg Pomerantzeff and assigned to the same assignee as is the present invention. In the Pomerantzeff system, the lower power CW laser is brought to focus at the nodal point of the patient's eye, a feature which cannot be employed with high power lasers for fear of damage to the eye. Moreover, in the Pomerantzeff system an ophthalmoscopic lens creates an aerial image of the fundus which is observed, illuminated and treated; such aerial images should be avoided in high power laser systems because focusing such lasers in air degrades the quality of the surgical beam. In addition, the use of low power lasers in the Pomerantzeff system does not require that the eyes of the observer be protected.

OBJECTS AND SUMMARY OF THE INVENTION

It is an object of the present invention to provide an apparatus for focusing high power laser pulses coincident with the center of the field of observation of a biomicroscope at a surgical site.

It is another object of the present invention to provide an apparatus for protecting the eyes of a biomicroscope observer in a system wherein high energy laser pulses are delivered into the center of the field of observation of the biomicroscope.

Still another object of the present invention is to provide a mobile apparatus which permits high power laser pulses to be focused into the center of a biomicroscope field of observation.

In accordance with the present invention an apparatus is provided to which a biomicroscope can be secured at one side. An objective lens is mounted on the other side so that the biomicroscope observation path passes through the lens and is focused at the surgical site. The apparatus is also arranged to receive high power laser pulses along a laser beam delivery path which intersects the reflecting surface of a dichroic mirror disposed inside the apparatus. The mirror is selectively movable in three dimensions to direct the laser pulses through the objective lens and into focus at the surgical site in the center of the biomicroscope observation field. The mirror is mounted on a shaft which is movable longitudinally of its axis, rotationally about its axis and pivotally about a point on its axis.

A shutter mechanism is provided in the biomicroscope observation path to protect the eyes of an observer. The shutter is normally open and is synchronized with the generation of each laser pulse to close for the duration of that pulse.

The apparatus, which contains only the mirror, the mechanism for moving the mirror and the objective lens, is easily transported about any medical facility.

BRIEF DESCRIPTION OF THE DRAWINGS

These and other objects, features and many of the attendant advantages of the invention will be better understood upon a reading of the following detailed description when considered in conjunction with the accompanying drawings wherein like parts in each of the several figures are identified by the same reference numerals, and wherein:

FIG. 5 is an exploded view in perspective of the mirror movement control mechanism employed in the embodiment of FIGS. 2, 3 and 4.

DESCRIPTION OF THE PREFERRED EMBODIMENT

Figure 1:
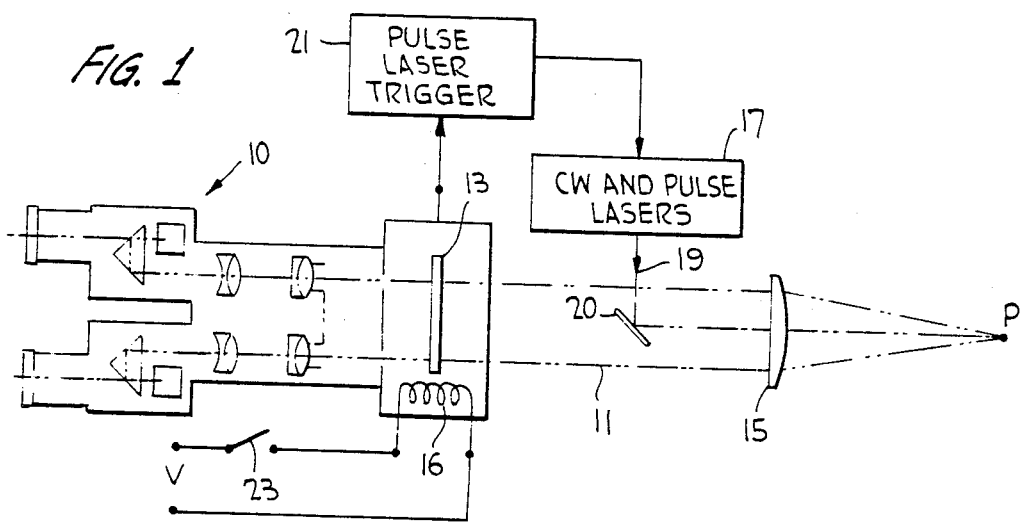
FIG. 1 is a schematic diagram of a system for performing surgery with high power laser energy in accordance with the present invention.

The diagram of FIG. 1 schematically illustrates the operation of the system of the present invention. A biomicroscope is generally designated by the reference numeral 10 and has an observation path 11 which passes through a selectively closable shutter mechanism 13. The observation path 11 is focused by an objective lens 15 to a point P corresponding to the side of a surgical procedure. Point P is located anterior of the retina of the eye in optical surgery. A laser beam is delivered from a laser assembly 17 which is designated in FIG. 1 as including both a CW laser and a pulse laser. The CW laser is utilized for aiming purposes only and not for treatment of the tissue during the surgical procedure. Both the lower power CW beam and the high power pulse beam are provided along the same laser beam delivery path 19 at separate times, depending upon whether the system is in the focusing or operating mode. The laser beam delivery path intersects the reflective surface of a mirror 20 which, as described below, is movable in three separate dimensions to deflect the laser beam through the objective lens 15 and into focus at the surgical site point P. The individual laser pulses are triggered from a pulse laser trigger circuit generally designated by the reference numeral 21.

The biomicroscope 10 is a conventional biomicroscope such as any one of the many types manufactured by the Carl Zeiss Company of New York. Such biomicroscopes are conventionally utilized in ophthalmic surgical procedures.

Shutter 13 is part of a large-aperture shutter assembly wherein the shutter is controlled by an electromagnetic solenoid 16. Such shutter assemblies are commercially available and may take the form of the shutter unit designated by the model number 1142042 manufactured by the Prontor Werks Company of West Germany.

As schematically illustrated in FIG. 1, a switch 23 is actuable to apply a voltage across solenoid 16 to close shutter 13. This same voltage is applied from the shutter assembly to the pulse laser trigger unit 21 to trigger the pulse laser and generate a high power output pulse along the beam delivery path 19. The shutter is thereby closed upon generation of each laser pulse so that the eyes of the observer through the biomicroscope 10 are protected. It is to be understood, of course, that switch 23 is merely a schematic representation of the precise circuitry employed to operate the pulse laser and the shutter 13 is synchronization. More particularly, switch 23 may actually be a repetitive on-off device which effects operation of the shutter and the pulse laser. The normally open shutter is closed for approximately one hundred milliseconds and contains contacts which supply the necessary voltage to fire the laser upon shutter closure. This assures that the shutter has been closed before the laser pulse can be generated.

As noted above, the path to be followed by the high energy laser pulses can be initially established by a coaxial low energy CW laser beam. The collimated high energy pulses and the collimated aiming beam are delivered to the unit described below with commercially available guides. The incoming laser beams are introduced into the unit between the objective lens and the shutter. Mirror 20 steers the laser beam through the objective lens 15 to the center of the field of observation. The biomicroscope has infinity-corrected optics so that the coherent laser beam and the observation path focus at the same point.

As noted above, the microscope 10 is a conventional microscope which includes a pair of eyepieces and internal optics for directing light from objective lens 15 towards the eyepieces. Such microscopes have adaptive connections for shutters, such as shutter 13.

Figure 2:
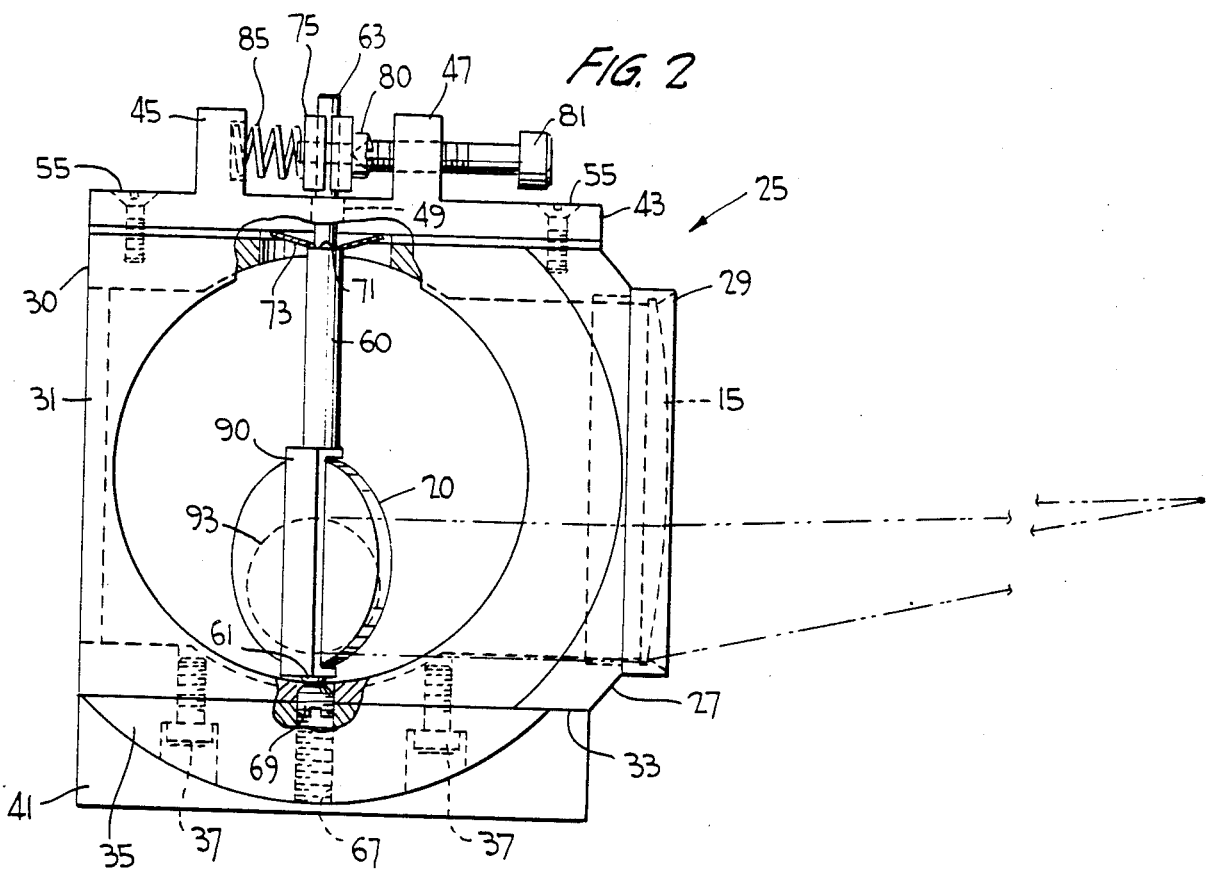
FIG. 2 is a side view in elevation of apparatus constructed in accordance with the present invention.
Figure 3:
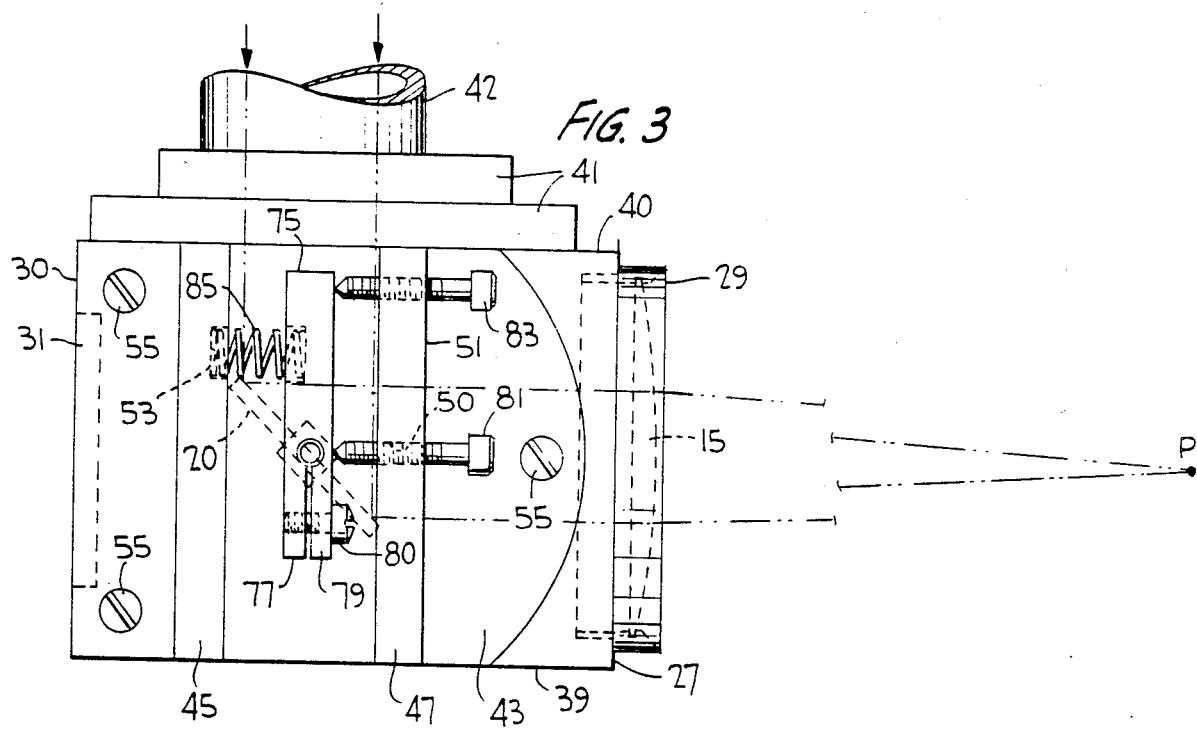
FIG. 3 is a top view in plan of the apparatus of FIG. 2.
Figure 4:
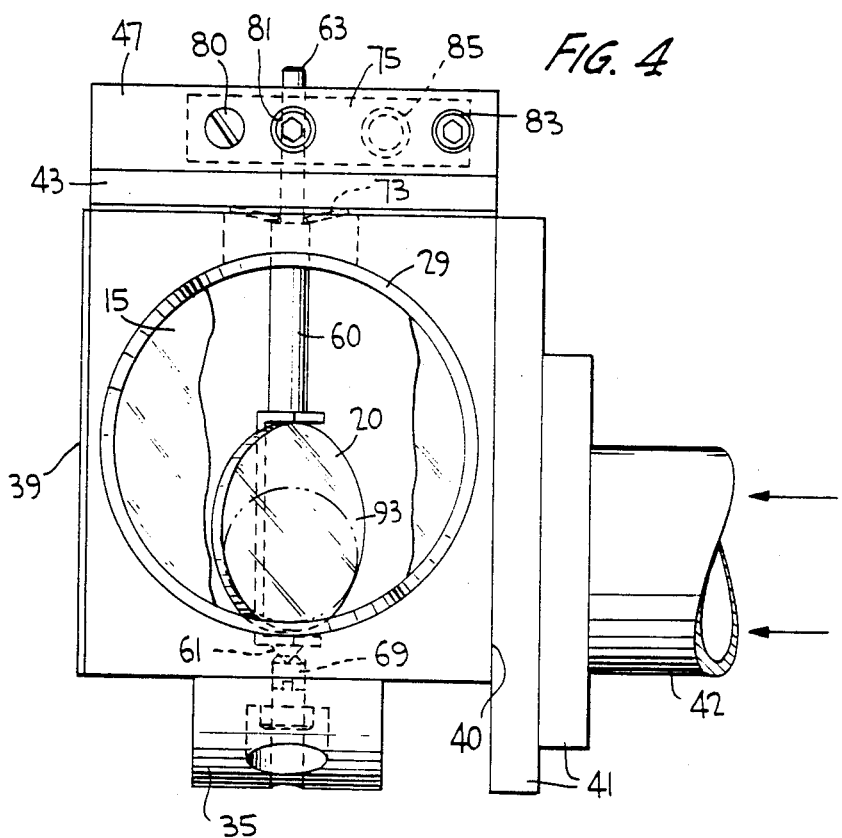
FIG. 4 is a front view in elevation of the apparatus of FIG. 2.

The unit which steers the laser beam into the observation field of the biomicroscope is illustrated in detail in FIGS. 2-4 to which specific reference is now made. The unit comprises the housing generally designated by the reference numeral 25. Housing 25 has a front wall 27 which terminates in a lens mount frame 29 in which the objective lens 15 is mounted. A rear wall 30 is disposed on the opposite side of housing 25 from front wall 27 and is provided with a mounting opening 31 which receives the biomicroscope/shutter arrangement. With the biomicroscope 10 and shutter 13 thus connected at mounting opening 31, the observation path 11 of FIG. 1 passes directly through the housing 25 through the rear wall 30 and fron wall 27.

Housing 25 has a bottom wall 33 to which a biomicroscope tilt member 35 is secured by means of screws 37. The tilt mounting element 35 is an arcuate member having a concave surface disposed below the unit housing to permit the concave surface to be slid with respect to an abutting convex surface (not shown) so that the entire housing 25 and the attached biomicroscope assembly can be tilted in a plane which is prependicular to the front wall 25, the rear wall 30 and the bottom wall 33. In this manner, the field of observation 11 of FIG. 1 can be tilted up and down as desired. In addition, a transverse rotation mechanism (not shown) may be provided to permit selective transverse movement of the observation field.

One side wall 39 of the housing 25 is generally rectangular and is removed in the view illustrated in FIG. 2 for purposes of clarity. The other opposite side wall 40 has a coarse adjustment mount 41 secured thereto for adjusting the laser beam direction to clear the objective lens aperture. More specifically, the mounting unit 41 comprises two mutually slidable plates, the outer one of which is secured to an articulated arm 42 which serves as a guide for the laser beam received from the lasers 17 of FIG. 1. The articulated arm 42 can thus be moved vertically (as viewed in FIG. 4; in and out of the plane of the paper as viewed in FIG. 3) to adjust the laser beam delivery path height in housing 25.

The open top of housing 25 is covered by a cover plate 43 having two upstanding flanges 45 and 47 extending transversely of the housing (i.e., between side walls 39 and 40) in parallel spaced relation. A slot 49 is defined through the cover plate 43 at a location which is disposed between the two flanges 45 and 47 and substantially transversely centered with respect to the sides of the plate. Slot 49 has an elongated or longitudinal dimension which is perpendicular to the two flanges 45 and 47. Flange 47 has two transversely spaced but longitudinally-extending threaded bores 50 and 51 defined therethrough. Threaded bore 50 is defined along the center line of the unit so as to be aligned with slot 49 in the coverplate 43. Threaded bore 51 is transversely spaced from threaded bore 50 and is closer to side wall 40 of housing 25 than to side wall 39. Flange 45 has a longitudinally-extending recess 53 defined therein at a surface which faces flange 47. The transverse location of recess 53 is intermediate the threaded bores 50 and 51. Coverplate 43 is secured to the top of housing 25 by means of screws 55 or the like.

Referring to FIG. 5 in conjunction with FIGS. 2-4, the coverplate 43 is part of an assembly whereby the dichroic mirror 20 of FIG. 1 may be moved in three dimensions to focus the laser beam through objective lens 15 and unto the surgical site at point P. Specifically, a shaft 60 has a generally convex mounting bearing 61 at its bottom end and a generally cylindrical portion 63 of reduced diameter at its top end. Shaft 60 is disposed within housing 25 with convex bearing 61 projecting into a threaded aperture 67 that extends through the bottom wall 33 of the housing and into alignment with a similar threaded bore 67 in the microscope tilt mounting assembly 35. An adjustment screw 69 is threadedly engaged in bores 67 and 65 so that its distal end 70 contacts the convex bearing 61. To this end, the distal end 70 of the adjustment screw 69 is made concave to serve as a bearing pad for receiving the convex bearing. In the embodiment illustrated in FIGS. 2–5, the convex bearing 61 is actually of a generally conical configuration and bearing pad surface 70 is contoured to mate therewith to permit rotation and pivoting of the shaft 60 within housing 25.

The reduced diameter cylindrical portion 63 at the top end of shaft 60 is set off from the remainder of the shaft by an annular shoulder 71 which faces generally upward toward the top wall of the housing. A Belleville washer 73 or other resilient type retainer is placed about shaft section 63 at shoulder 71 which serves as a stop for the washer 73. The washer 73 is resiliently compressed by shoulder 71 against the underside of coverplate 43 so as to force the bearing 61 against the bearing surface 70 at the bottom of the shaft. The reduced diameter cylindrical portion 63 of shaft 60 extends through slot 49 in coverplate 43 into the region between flanges 45 and 47. The dimensions of slot 49 are such as to preclude transverse movement of the shaft in slot 49 but to permit longitudinal movement of the shaft therein. In other words, the transverse dimension of slot 49 is substantially equal to or just slightly greater than the diameter of the top portion 63 Of shaft 60 so that the shaft cannot move in a direction parallel to the flanges 45 and 47. The longitudinal dimension, however, of slot 49 is on the order of twice the diameter of the reduced portion 63 of shaft 60 so that there is slack for the shaft to pivot in slot 49 about the bearing 61 in bearing pad 70.

A bracket member 75 is in the form of a solid block which is disposed between flanges 45 and 47 above top plate 43. Bracket member 75 has a vertically extending through bore 76 adapted to receive the portion 63 of shaft 60 which is exposed above the top plate 43. Bracket member 75 is bifurcated from bore 76 to one of the ends of the bracket member to form two sections 77 and 79. A threaded bore 78 extends through both sections 77 and 79 in a longitudinal direction and receives a screw 80 which permits the two sections 77 and 79 to be tightened against one another. With the two sections thus tightened, the shaft portion 63 in bore 76 is firmly engaged within the bracket member 75. Two adjustment screws 81 and 83 are received in respective threaded bores 50 and 51 in bracket member 47 and have their distal ends bearing against bracket member 75. A coiled compression spring 85 is partially disposed in recess 53 of flange 45 and serves as a bias member in urging bracket member 75 away from flange 45 and toward flange 47. The distal end of screws 81 and 83, therefore, oppose the bias force or resilient urging of spring 85 to establish the position of bracket member 75 between the two flanges 45 and 47. Screw 81 is longitudinally displaceable along an axis which is perpendicular to the axis of shaft 60 so that the shaft can be tilted in a vertical plane about bearing 61 in bearing pad 70 by a movement of screw 81 in and out of its threaded bore 50 against the urging of spring 53. Screw 83, on the other hand, is displaced from the axis of shaft 60 so that it exerts a turning torque on bracket member 75 so that the shaft may be rotated about its axis in response to the longitudinal displacement of adjustment screw 83.

Mirror 20 is a dichroic mirror in the shape of circular disc which is secured to a mirror-mounting portion 90 of shaft 60. This mirror-mounting portion is configured in a generally C-shape with bearing member 61 projecting from its lower portion. The mirror-mounting portion 90 of the shaft has a generally rectangular vertically-extending section to which the mirror 20 is secured by means of cement 91, or the like. When the mirror is secured in the mirror-mounting portion 90, the reflective surface of the mirror resides in a plane which contains the longitudinal axis of shaft 60. In other words, the vertically extending portion of the mirror-mounting section is off-axis with respect to the shaft so that the shaft axis can be coplanar with the reflective surface of the mirror.

In setting up the apparatus for operation, the position of the laser beam is adjusted by means of the coarse laser adjustment mechanism 41 until the beam image 93 is fully received at the reflecting surface of mirror 20. The mirror image 93 is quite wide at this point to avoid burnout of the mirror and objective lens. The reflecting surface of the mirror is preferably somewhat larger than the image 93 of the laser beam, as illustrated, so that the setup procedure for proper positioning of the image 93 on the mirror's surface is relatively easy. For purposes of these adjustments, of course, the low power CW laser beam is employed; since both the low power CW laser and the high power pulse laser follow the same path, focusing of the low power laser beam will have the effect of proper focusing of the high power laser pulses. Once the position of the laser beam on the mirror is set so that the collimated beam falls inside the aperture of objective lens 15, the height of the mirror can be adjusted by properly adjusting set screw 69. This has the effect of moving the shaft 60 and mirror 20 up or down to balance the resilient urging force exerted by the Belleville washer 73. The elevation angle or tilt of the laser beam is then adjusted by adjusting screw 81 to attain the desired tilt of mirror 20 and shaft 60 about bearing 61. The angular position of the mirror about the axis of shaft 60 is adjusted by simultaneously rotating screws 81 and 83 until the laser beam is centered in the observation field.

The capability of adjusting the dichroic mirror 20 permits the incoming laser pulses to be directed precisely to a predetermined location within the field of observation. The large laser beam diameter can be handled by the conventional high quality objective lens 15 because of the relatively low power density of the large diameter beam. The path of the high energy laser pulses, as described above, is identified initially by the CW low energy laser beam. The collimated high energy pulse and the collimated aiming CW beam are delivered into the housing 25 using commercially available guides. For example, conventional gold-plated tubes are employed to guide the laser beams with dichroic mirrors at every rotating joint to provide six degrees of freedom. The mirror steers the inserted laser beam through the objective lens 15 to the center of the field of observation of the biomicroscope 10. Since the biomicroscope is infinity-corrected optically, both the coherent laser beam and the observation path focus at the same point.

It is to be noted that a common final objective lens 15 is employed for focusing both the visual path of the biomicroscope as well as the laser path which performs the surgical procedure. The particular objective lens which is employed is an air-spaced doublet, such as sold by the Carl Zeiss Company for clinical biomicroscopes. This permits a simple positional adjustment of the dichroic mirror 20 to place the area to be treated at any desired location in the visual field. Since the doublet lens is corrected for best focus of light rays traversing it off axis, the best possible focus is attained without resorting to using separate focusing objective lenses for the biomicroscope and the laser.

The dove-tailing of the observation path and the laser beam delivery path permits portability and interchangeability of the laser delivery system with slit lamp biomicroscopes or operating microscopes. This feature permits the user to attach the delivery system to the housing at different work stations.

The use of a high-quality, inverted action shutter to protect the observer's eyes is an improvement over prior art beam choppers, such as slotted disks, conventionally used for continuously running, repetitively pulsed lasers. Because the shutter has a built in "shutter closed" monitor switch, it permits contact within the shutter to provide a signal to the laser power supply that triggers the single laser pulse. The use of the inverted action shutter is an improvement over filters, such as used in prior art systems, in that the presence of a filter alters the color and dims the image of a target tissue.

It must be stressed that the present invention distinguishes over the system described in the aforementioned Pomerantzeff patent application in that the Pomerantzeff system relates to photocoagulation of the retina and is assembled to reduce astigmatism in viewing the retina. The present invention is intended to treat structures of the eye located anterior to the retina. In addition, the Pomerantzeff system is designed to pass laser irradiation through the nodal point of the crystalline lens of the eye as it traverses the path to the posterior segment of the eye. The present invention employs infinity-corrected optics, available commercially, for the observation system and the image of the target is not brought to focus at any location between the target and the observer's eyes. The Pomerantzeff system, on the other hand, employs aerial images and the retinal target is imaged at five locations.

It must be stressed that the present invention relates to the delivery of high powered laser pulses to targets anterior to the retina as opposed to low power CW laser beams focused at the nodal point of the eye. The present invention provides three degrees of freedom of mirror motion whereas in the aforesaid Pomerantzeff patent application, the mirror is fixed at a conjugate point relative to the nodal point of the eye and thereby has only two degrees of freedom.

Having described a specific embodiment of a new and improved optical coupling device for a biomicroscope constructed in accordance with the present invention, it is believed that other modifications, variations and changes will be suggested to those skilled in the art of the above teachings. It is therefore to be understood that all such variations, modifications and changes are believed to fall within the scope of the invention as defined in the appended claims.

What is claimed is:

1. Apparatus for use in conjunction with a biomicroscope and a pulsed laser for delivering high power laser pulses to a living tissue site to effect medical treatment of that tissue, the apparatus comprising:
   a housing;
   mounting means for securing said biomicroscope to said housing to establish an observation path for said biomicroscope through said housing;
   an objective lens secured to said housing in said observation path for focusing said observation path at said living tissue site;
   means for delivering said high power laser pulses into said housing along a first laser beam delivery path;
   a mirror assembly disposed in said housing and having a reflective surface disposed along said first laser beam delivery path for reflecting said high power laser pulses along a second laser beam delivery path extending through said objective lens, said mirror assembly further comprising means for selectively positionally controlling said reflective surface in each of three different directions to direct said high power pulses to be focused by said objective lens at said tissue site;
   wherein said mirror assembly includes:
   a shaft having: a longitudinal axis, a generally cylindrical portion at a first end, a pivot bearing at a second end, said pivot bearing having a generally convex configuration, and a mirror mounting section disposed intermediate said first and second ends and mounting said reflective surface;
   shaft receiving means in said housing for receiving said generally cylindrical portion of said shaft in a journal-type engagement to permit rotation of said shaft about said longitudinal axis; and
   a bearing pad secured to said housing and urged axially against said pivot bearing at said second end of said shaft.

2. The apparatus according to claim 1 wherein said observation path and said second laser beam delivery path are coincident only at said tissue site.

3. The apparatus according to claim 1 further comprising:
   shutter means for said biomicroscope disposed in said observation path between said mounting means and said objective lens to alternatively block and pass light along said observation path;
   means for selectively generating said high power laser pulses; and
   means synchronized to generation of each laser pulse for closing said shutter means to protect the eyes of an observer through said biomicroscope from damage caused by the high power laser pulses.

4. The apparatus according to claim 1 wherein said objective lens is positioned relative to said mounting means to provide focusing of the tissue site only at the eyes of the observer along said observation path.

5. The apparatus according to claim 1 further comprising longitudinal bias means secured to said housing for resiliently urging said shaft generally longitudinally in a direction away from said first shaft end and toward said second shaft end; and
   wherein said bearing pad is a screw member threadedly received in said housing for axial displacement generally longitudinally against said second end of said shaft to permit selective longitudinal displacement of said shaft against said longitudinal bias means.

6. The apparatus according to claim 5 further comprising:

a bracket member secured to said cylindrical portion of said shaft at said first shaft end;

transverse bias means secured to said housing for resiliently urging said bracket member in a direction perpendicular to said longitudinal axis and parallel to said observation path; and first adjustment means for selectively applying a first force to said bracket member in a direction which is perpendicular to and intersects said longitudinal axis to effect selective displacement of said bracket member and said first shaft end against the resilient urging of said transverse bias means to permit selective tilting of said shaft about said second shaft end.

7. The apparatus according to claim 6 further comprising second adjustment means for selectively applying a second force to said bracket member in a direction which is parallel to said first force and skewed with respect to said longitudinal axis for selectively pivoting said bracket member and said shaft about said longitudinal axis.

8. The apparatus according to claim 7 wherein said first and second adjustment means comprise first and second screws threadedly engaged in and having distal ends projecting from a support block, the distal ends of the screws bearing against the bracket member to oppose the resilient urging of said transverse bias means.

9. The apparatus according to claim 5 further comprising:

a bracket member secured to said cylindrical portion of said shaft at said first shaft end;

transverse bias means secured to said housing for resiliently urging said bracket member in a direction perpendicular to said longitudinal axis and parallel to said observation path; and adjustment means for selectively applying a force to said bracket member at a pivot point which is radially displaced from said longitudinal axis and in a direction generally opposite the resilient urging of said transverse bias means to permit selective rotation of said bracket member and said shaft about said longitudinal axis.

10. The apparatus according to claim 5 wherein said shaft includes an annular shoulder and wherein said longitudinal bias means comprises a resilient washer disposed about said shaft at said shoulder and having a radially inner edge contacting said shoulder and a radially outer edge contacting said housing.

11. The apparatus according to claim 1 further comprising:

a bracket member secured to said cylindrical portion of said shaft at said first shaft end;

transverse bias means secured to said housing for resiliently urging said bracket member in a direction perpendicular to said longitudinal axis and parallel to said observation path; and first adjustment means for selectively applying a first force to said bracket member in a direction which is perpendicular to and intersects said longitudinal axis to effect selective displacement of said bracket member and said first shaft end against the resilient urging of said transverse bias means to permit selective tilting of said shaft about said second shaft end.

12. The apparatus according to claim 11 further comprising second adjustment means for selectively applying a second force to said bracket member in a direction which is parallel to said first force and skewed with respect to said longitudinal axis for selectively pivoting said bracket member and said shaft about said longitudinal axis.

13. The apparatus according to claim 1 further comprising:

a bracket member secured to said cylindrical portion of said shaft at said first shaft end;

transverse bias means secured to said housing for resiliently urging said bracket member in a direction perpendicular to said longitudinal axis and parallel to said observation path; and adjustment means for selectively applying a force to said bracket member at a pivot point which is radially displaced from said longitudinal axis and in a direction generally opposite the resilient urging of said transverse bias means to permit selective rotation of said bracket member and said shaft about said longitudinal axis.

14. The apparatus according to claim 1 wherein said reflective surface is a dichroic mirror.

15. The apparatus according to claim 7 further comprising a low power laser means for delivering a low power aiming beam along a path which reflects off said reflective surface and impinges upon said tissue site to establish said first and second delivery paths for said high power laser pulses.

* * * * *